(12) United States Patent
Price

(10) Patent No.: US 9,500,638 B2
(45) Date of Patent: Nov. 22, 2016

(54) METHOD OF MEASURING WATER CONTAMINATION IN TURBINE AND OTHER INDUSTRIAL OILS

(71) Applicant: Spectro Sciencific, Inc., Chelmsford, MA (US)

(72) Inventor: Randi Price, Westborough, MA (US)

(73) Assignee: Spectro Scientific, Inc., Chelmsford, MA (US)

( * ) Notice: Subject to any disclaimer, the term of this patent is extended or adjusted under 35 U.S.C. 154(b) by 0 days.

(21) Appl. No.: 14/619,245

(22) Filed: Feb. 11, 2015

(65) Prior Publication Data

US 2016/0231304 A1    Aug. 11, 2016

(51) Int. Cl.
G01N 31/00 (2006.01)
G01N 33/03 (2006.01)
G01N 33/26 (2006.01)
G01N 33/28 (2006.01)
G01J 3/42 (2006.01)
G01J 3/10 (2006.01)

(52) U.S. Cl.
CPC ........... *G01N 33/2847* (2013.01); *G01J 3/108* (2013.01); *G01J 3/42* (2013.01)

(58) Field of Classification Search
CPC ....... G01N 31/00; G01N 33/03; G01N 33/26
USPC .......... 436/60, 40, 41, 42; 210/643; 702/28; 250/301, 255
See application file for complete search history.

(56) References Cited

U.S. PATENT DOCUMENTS

| 4,434,233 | A | * | 2/1984 | Bzdula .......................... 436/60 |
| 5,306,909 | A | * | 4/1994 | Jones et al. ................... 250/255 |
| 5,381,002 | A | * | 1/1995 | Morrow et al. .............. 250/301 |
| 8,068,218 | B2 | | 11/2011 | Higgins et al. |
| 8,384,495 | B2 | | 2/2013 | Albin et al. |
| 2009/0194480 | A1 | * | 8/2009 | McDaniel et al. ............ 210/643 |
| 2009/0257047 | A1 | * | 10/2009 | Higgins et al. ................. 356/51 |
| 2011/0320135 | A1 | * | 12/2011 | van de Voort et al. ......... 702/28 |

OTHER PUBLICATIONS

Araujo et al., Evaluation of Water Content and Average Droplet Size in Water-in-Crude Oil Emulsions by Means of Near-Infrared Spectroscopy; Energy & Fuels, 2008 pp. 3450-3458.
Aquastar, Karl Fisher Titration Basics, EMD Chemicals, Inc. 480 South Democrat Road, Gibbstown, NH 08027 https://www.emdmillipore.com/US/en/lab-technical-resources/karl-fischer-faqs/w5yb.qB.0VgAAAFE3oMWq.DH,nav; Copyright 2015.

* cited by examiner

*Primary Examiner* — Brian J Sines
(74) *Attorney, Agent, or Firm* — Iandiorio Teska & Coleman, LLP

(57) ABSTRACT

A method of determining the amount of water in an industrial oil (e.g., turbine oil) includes homogenizing an oil sample, subjecting the homogenized sample to infrared spectroscopy within 30 minutes of homogenization, and determining a baseline absorbance level for the sample within a predetermined wavenumber range. That baseline is compared with spectral template baselines and, based on the comparison, the amount of water in the oil sample is estimated.

11 Claims, 4 Drawing Sheets

METHOD OF MEASURING WATER CONTAMINATION IN TURBINE AND OTHER INDUSTRIAL OILS

FIELD OF THE INVENTION

This invention relates to a method of determining an amount of a polar substance in a non-polar media sample.

BACKGROUND OF THE INVENTION

Water in industrial oils (e.g., turbine oils) is problematic and can cause equipment failure. Accordingly, the oil is periodically analyzed to determine the water content and to schedule equipment oil changes. The usual analysis method is the Karl Fischer coulometric titration method. This method, however, is time consuming, somewhat cumbersome, and requires hazardous reagents, careful sample preparation, expensive equipment, and training.

Infrared spectroscopy, if used to measure the amount of water in oil, can produce inaccurate results. See U.S. Pat. No. 8,068,218 incorporated herein by this reference. Water can scatter the infrared light, the size of the water droplets can vary, and the water can separate from the oil in a sample all leading to variability when infrared spectroscopy is used. In the '218 patent, a surfactant is added to the oil sample to disperse the water in the oil and increase its optical absorbance. Still, the infrared bands associated with water absorbance may be highly variable with the type of oil sample and its chemical state at the time of water ingression.

See also Araujo et al., *Evaluation of Water Content and Average Droplet Size in Water-in-Crude Oil Emulsions by Means of Near-Infrared Spectroscopy*, Energy and Fuels 2008, pages 3450-3458, by The American Chemical Society (incorporated herein by this reference) where a homogenizer is used to create artificial samples to prove the principle of measuring the amount of water in crude oil in-situ. However in this case the homogenization technique is only used to create representative artificial samples. The oil analyzed was not homogenized.

SUMMARY OF THE INVENTION

Featured is a new method for analysis of water contamination in turbine oils, other oils, and other fluids which is robust and reliable. In one preferred method, the sample is homogenized and then subject to infrared spectroscopy where the baseline of the resulting optical spectrum exiting the sample is compared to the baselines of a number of spectral templates.

Featured is a method of determining an amount of a polar substance (e.g., water) in a non-polar media sample (e.g., oil). The method comprises homogenizing the sample. Then, using a spectrometer device, an optical spectrum is passed through the sample and the resulting optical spectrum exiting the sample is detected. A baseline of the resulting optical spectrum is related to a predetermined set of spectras of known concentrations of the polar substance in the non-polar media. The concentration of the polar substance in the non-polar media sample is then determined based on the relation of the baseline of the resulting optical spectrum to a baseline of a predetermined spectra.

The steps after homogenizing are preferably carried out within 30 minutes and, even more preferably, within 10 minutes. Homogenizing preferably includes using a homogenizer introduced into the sample and energized for at least 30 seconds.

In one embodiment, passing the optical spectrum includes directing infrared radiation to the sample and detecting the resultant optical spectrum exiting the sample includes analyzing absorbance over wavelengths from about 2.5 to about 3.5 microns in the detected optical spectrum.

The predetermined set of spectras of known concentrations of the polar substance in the non-polar media are preferably produced by determining the concentration of a polar substance in a non-polar media sample using the Karl Fischer coulometric titration method, homogenizing the sample, passing an optical spectrum through the sample, detecting the resultant optical spectrum exiting the sample, and storing data concerning the resultant optical spectrum and the determined concentration. The predetermined set of spectras preferably includes stored spectras for different oils from different manufacturers and even different types of oils available from different manufacturers.

In another version, the predetermined spectra of known concentrations of the polar substance in the non-polar media are produced by adding a known concentration of the polar substance to a non-polar media sample, homogenizing the sample, passing an optical spectrum though the sample, detecting the resultant optical spectrum exiting the sample, and storing data concerning the resultant optical spectrum and the known concentration.

Also featured is a method of determining the amount of water in an industrial oil including homogenizing the oil sample, subjecting the homogenized sample to infrared spectroscopy within 30 minutes of homogenization, determining a baseline absorbance level for the sample within a predetermined wavenumber range, and comparing said baseline with spectral template baselines. Based on the comparison, the amount of water in the oil sample can be quantified.

One featured method includes determining the concentration of water in several samples using the Karl Fischer coulometric titration method, homogenizing each sample, passing an optical spectrum through each sample, detecting the resulting optical spectrum exiting each sample, and storing data concerning the resulting optical spectrums and the determined water concentration of each sample. Then, in use, a test oil sample with an unknown water concentration is homogenized. The method further includes passing an optical spectrum through this test sample, detecting the resulting optical spectrum exiting the test sample, and comparing the detected resulting optical spectrum of the test sample with the stored data. Based on the comparison, the water concentration of the test sample can be estimated.

One goal of the sample interaction with the homogenizer is to create evenly dispersed micro- or nanodroplets of water such that the probing infrared spectrum sees the water at every interrogation as a homogeneous scattering medium where the characteristic wavelength of the probing infrared spectrum has a nearly fixed ratio to the size of the droplets for a given characteristic oil type. In some cases, the probing radiation may be much larger than the droplets, which dictates the Rayleigh scattering regime, while in others the opposite might be true. As long as these ratios are consistent based on the oil type, the correct spectral templates may be applied to the analysis of the sample and quantitative water values reported.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
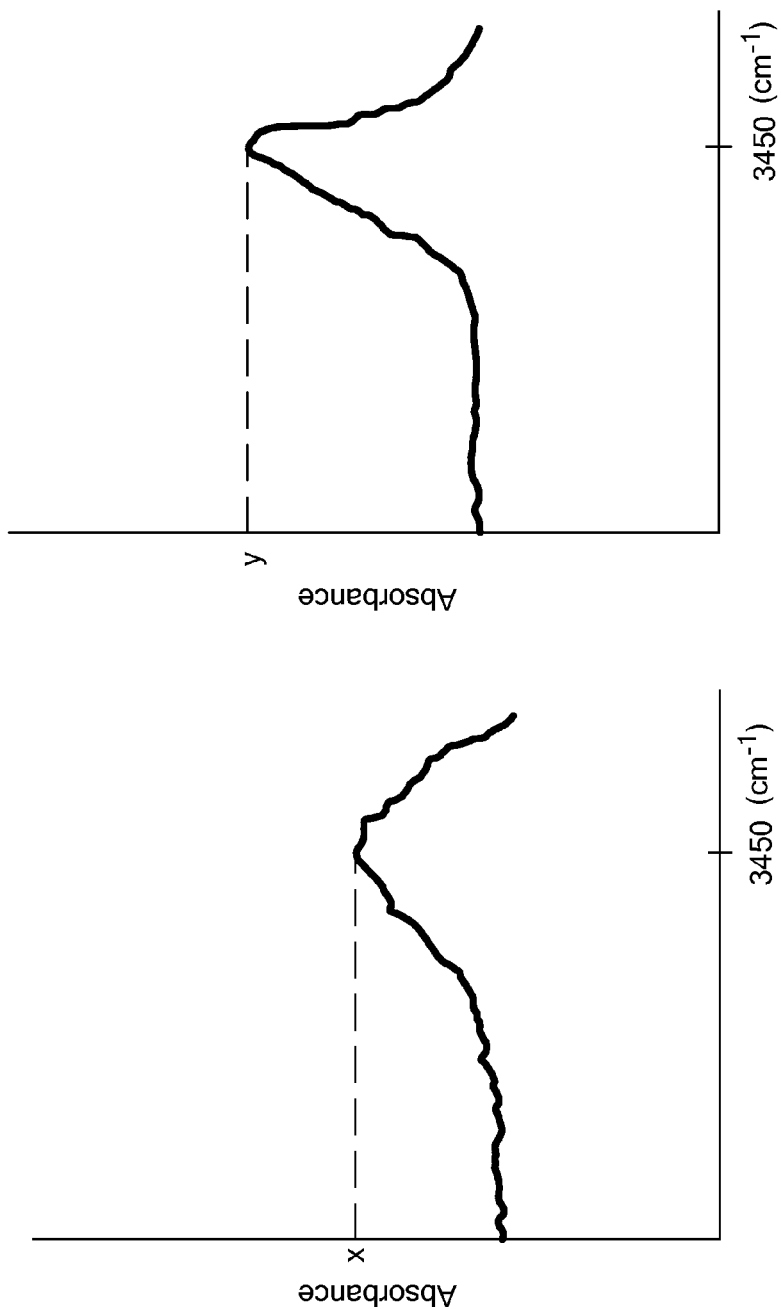
FIG. 1A is a plot showing absorbance versus wavenumber for a particular sample at one time.
FIG. 1B is a graph of absorbance versus wavenumber for the same sample at a second, different time showing the variability in measuring water contamination in turbine oil using infrared spectroscopy.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

As shown in FIGS. 1A and 1B, infrared spectroscopy of the same turbine oil sample at different times can result in different determinations concerning the parts per million water contamination of the turbine oil as shown as X in FIG. 1A and at Y in FIG. 1B. Turbine oils, especially, are formulated to have excellent water separation. So, the number of photons in an infrared spectroscopy measurement reaching the detector depends on how the water is physically dispersed in the oil. Over time, the number and size of discrete water droplets present in the oil can change. Given enough time, the water can even completely separate from the oil making it difficult to obtain an accurate measurement of the water content. Moreover, the peaks shown at X and Y where water absorbs infrared radiation (about 3,450 $cm^{-1}$) may not be as pronounced as depicted in the FIG. 1A or 1B and thus may be indistinguishable from noise. Thus, even if the peaks shown in FIGS. 1A and 1B were at the same or nearly the same absorbance level, they may be difficult to detect.

Figure 2:
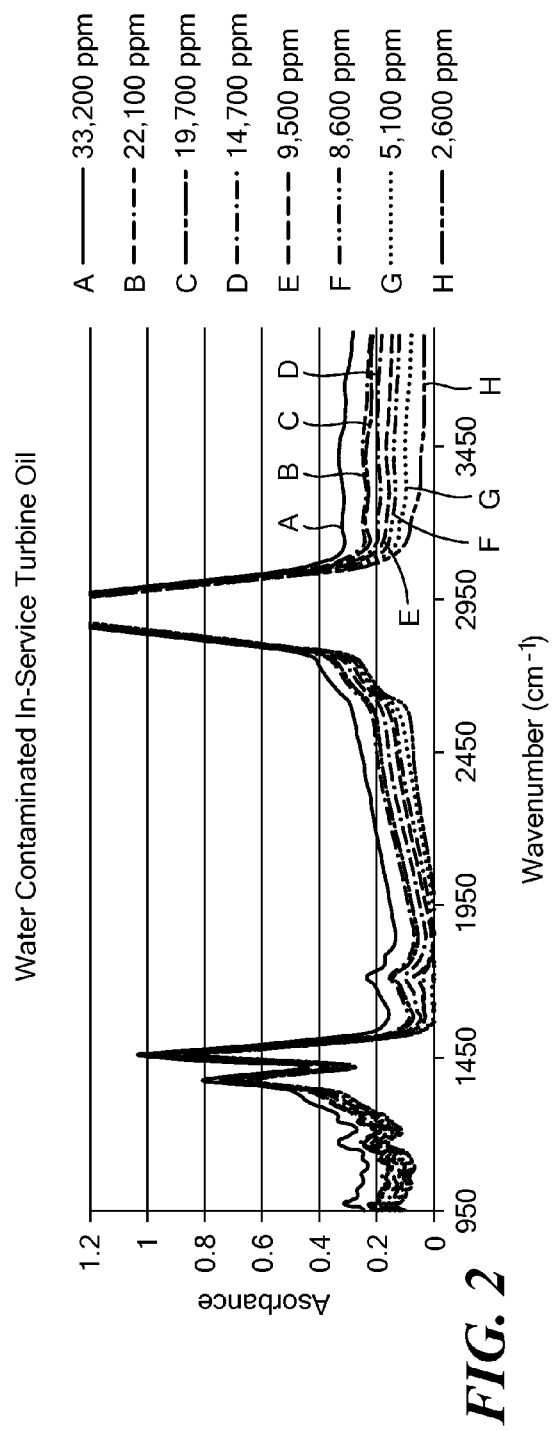
FIG. 2 is a graph showing absorbance versus wavenumber for a number of spectral templates generated in accordance with one example of a new method in accordance with the inventions.

In one example of the subject invention, spectral templates as shown in FIG. 2 are generated as follows. For one sample (e.g., one manufacturer's specific type turbine oil), the water concentration was determined using a proven procedure such as the Karl Fischer coulometric titration method. So, sample A was determined to have 33,200 ppm water contamination. This sample was then homogenized using a commercial homogenizer on high for thirty seconds. Within two to ten minutes after homogenization (no more that 30 minutes), the sample was subject to infrared spectroscopy using, for example, the Assignee's "Fluidscan" product (see U.S. Pat. No. 8,384,895 incorporated herein by this reference). Other spectroscopy devices and methods may be used. Typically, an optical spectrum is passed through the sample and the resultant optical spectrum exiting the sample is analyzed.

FIG. 2 shows the optical spectrum exiting the sample from sample A. This process is repeated for numerous samples B-H as shown in FIG. 2 containing different concentrations of water. Then, that process can be repeated for different type oils from the same manufacturer and for different type oils from different manufactures. Shell Oil, Inc., for example, may offer four or more different turbine oils.

The typical stored data associated with such spectral templates include the manufacturer name, oil designation (type), water concentration, and baseline. The baseline may only relate to a small number range, e.g., 3,000 to 4,000 $cm^{-1}$. Note that the baseline for sample A (33,200 ppm wave) is about 0.35 while the baseline for sample H is about 0.05. Such a baseline shift is indicative of the scattering of infrared light by microdroplets in this frequency regime—the more droplets of water present, the more scattering will occur, leading to an ever-increasing baseline shift. In other examples, the spectral templates of FIG. 2 are generated by introducing a known concentration of water to an oil sample, homogenizing the sample, subjecting the sample to infrared spectroscopy, and repeating this process for different concentrations of water in the oil. Modern spectrometers include a processor and memory so the spectral template data can be stored in the memory of the spectrometer.

Once the spectral templates have been generated and stored, turbine oil from a piece of equipment can be sumped and analyzed as follows. The first step is to enter the manufacturer name and oil designation, if known. Then, the sample is homogenized. Again, preferably a commercial grade homogenizer is introduced into the sample and energized for at least 30 seconds.

Figure 3:
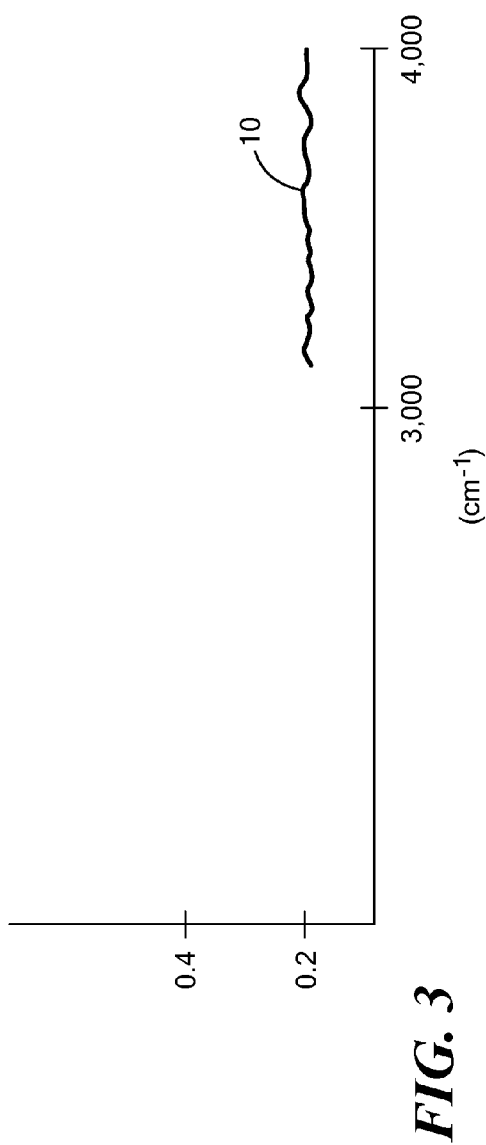
FIG. 3 is a graph showing absorbance versus wavenumber for a sample with an unknown water concentration in accordance with one method of the invention.

The sample will turn milky. Within two to thirty minutes (preferably less than ten minutes) after homogenization, the sample is subject infrared spectroscopy and the resulting optical spectrum exiting the sample may appear as shown at 10 in FIG. 3. The baseline of the spectrum between 3000 and 4000 $cm^{-1}$ is about 0.2. This baseline is related to the stored spectral templates of FIG. 2 and, based on the relation of the resultant spectrum at 10, FIG. 3 to stored spectral template D, FIG. 2, it is estimated that the sample under test has a water concentration of 14,700 ppm. If the Fluidscan product is used, the sample is presented to the flip top cell and the processor of the product is programmed to carry out the above method using instructions stored in memory.

Figure 4:
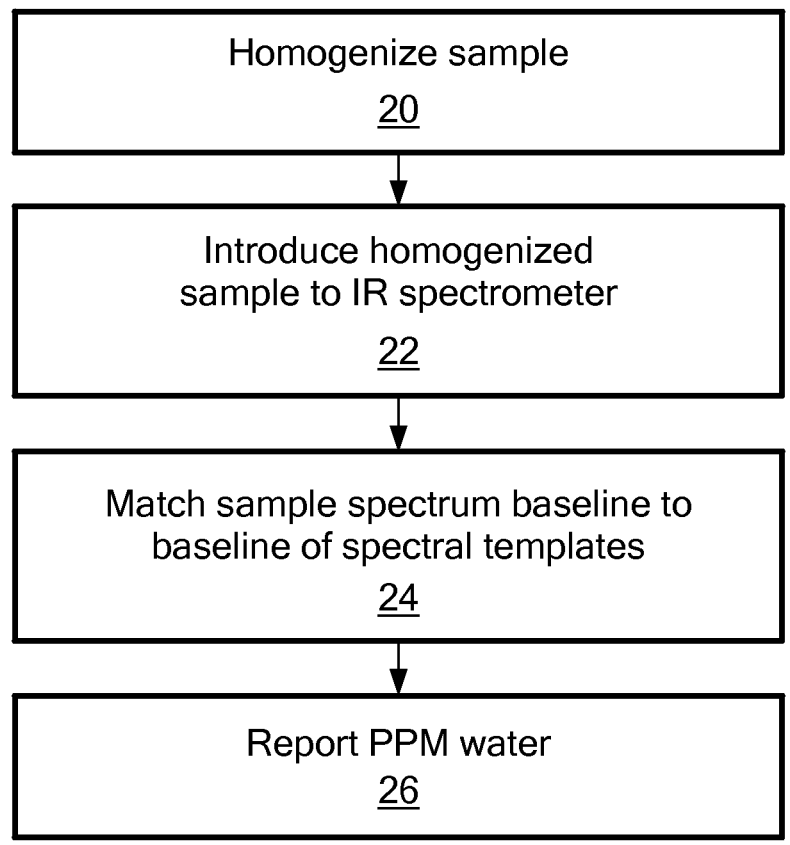
FIG. 4 is a flow chart depicting the primary steps associated with a method of determining an amount of a polar substance in a non-polar media sample in accordance with an example of the invention.

Thus, as shown in FIG. 4 the preferred method includes homogenizing the sample, step 20, introducing the homogenized sample to a infrared spectrometer, step 22, matching the sample spectrum baseline to the baseline of spectral templates stored in the system, step 24 and, based on a match found, estimating and reporting the water concentration as shown at step 26.

Figure 5:
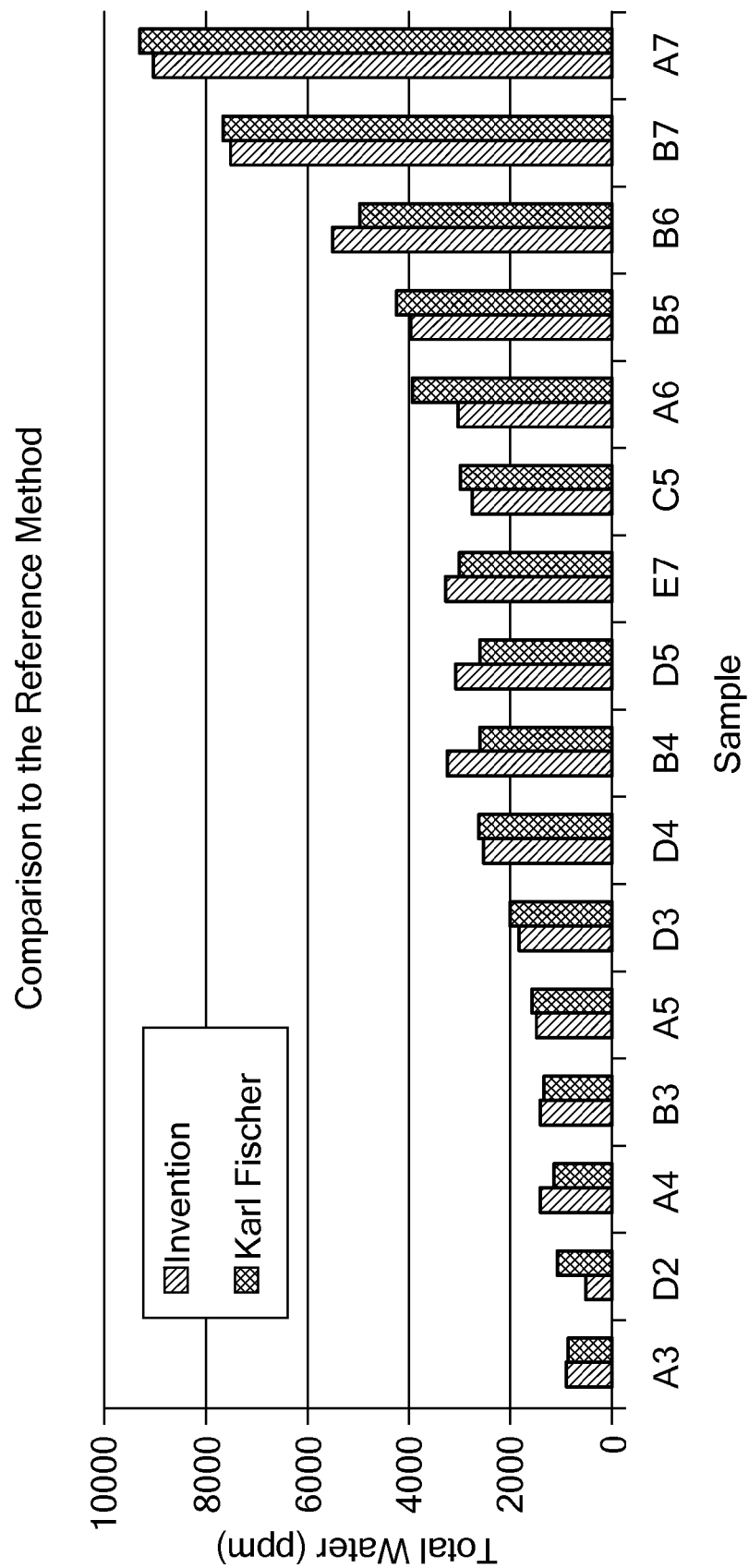
FIG. 5 is a graph showing parts per million water contamination in a turbine oil for a number of samples measured by the method featured in the subject invention as compared to the Karl Fischer coulometric titration method.

This method was carried out for several samples with water contamination levels ranging from 1,000 ppm to about 9,000 ppm and the same samples were analyzed using the Karl Fischer coulometric titration method. FIG. 5 shows a close correlation between the results obtained by the two different methods.

To demonstrate the importance of the homogenization step, another test included 13 in-service Chevron GST 32 oil samples from a power generation plant which were analyzed with and without proper homogenization. Several of the samples were homogenized for 30 seconds on high using a commercial homogenizer. Before analysis, the sample bottles were gently inverted 20 times to mix the samples. Another group of the samples were shaken vigorously by hand for 30 seconds and then left to sit for several minutes to allow air bubbles to dissipate. Before the analysis, these sample bottles were also gently inverted 20 times. In the second sample group, a commercial homogenizer was not used. The homogenized samples correlated closely to the Karl Fischer coulometric titration method while the shaken samples did not.

The result is a robust and reliable method capable of providing the user with an alert concerning a severe case of water contamination. The new method also provides an accurate determination of the total water contamination in an oil sample of about 100 ppm and above for all turbine oils analyzed via the processes described in the present invention.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. A method of determining an amount of a polar substance in a non-polar media sample, the method comprising:
   homogenizing the sample until it turns milky in appearance and the polar media in the sample is evenly dispersed as microdroplets or nanodroplets;
   passing an optical spectrum through the sample scattered by the microdroplets or nanodroplets;
   detecting the resulting optical spectrum exiting the sample;
   relating a baseline of the resulting optical spectrum to a predetermined set of spectras of known concentrations of the polar substance in the non-polar media; and
   determining a concentration of the polar substance in the non-polar media sample based on the relation of the baseline of the resulting optical spectrum to a baseline of a predetermined spectra;
   wherein no surfactant is added to the sample during the method.

2. The method of claim 1 in which the steps after homogenizing are carried out within 30 minutes.

3. The method of claim 1 in which the steps after homogenizing are carried out within 10 minutes.

4. The method of claim 1 in which homogenizing includes using a homogenizer introduced into the sample and energized.

5. The method of claim 4 in which the sample is homogenized for at least 30 seconds.

6. The method of claim 1 in which passing the optical spectrum includes directing infrared radiation to the sample.

7. The method of claim 6 in which detecting the resultant optical spectrum exiting the sample includes analyzing absorbance over wavelengths from about 2.5 to about 3.5 microns in the detected optical spectrum.

8. The method of claim 1 in which the predetermined set of spectras of known concentrations of the polar substance in the non-polar media are produced by:
   determining the concentration of a polar substance in a non-polar media sample using the Karl Fischer coulometric titration method,
   homogenizing the sample,
   passing an optical spectrum through the sample,
   detecting the resultant optical spectrum exiting the sample, and
   storing data concerning the resultant optical spectrum and the determined concentration.

9. The method of claim 1 in which the predetermined spectra of known concentrations of the polar substance in the non-polar media are produced by:
   adding a known concentration of the polar substance to a non-polar media sample,
   homogenizing the sample,
   passing an optical spectrum though the sample,
   detecting the resultant optical spectrum exiting the sample, and
   storing data concerning the resultant optical spectrum and the known concentration.

10. The method of claim 1 in which the predetermined set of spectras includes spectras for different oils from different manufacturers.

11. The method of claim 10 in which the predetermined set of spectras includes spectras for different types of oils available from at least one manufacturer.

* * * * *